United States Patent
Meskens

(10) Patent No.: US 9,592,395 B2
(45) Date of Patent: Mar. 14, 2017

(54) ELECTRICAL ISOLATION IN AN IMPLANTABLE DEVICE

(75) Inventor: Werner Meskens, Opwijk (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/555,317

(22) Filed: Jul. 23, 2012

(65) Prior Publication Data

US 2014/0025137 A1    Jan. 23, 2014

(51) Int. Cl.

| | | |
|---|---|---|
| *A61N 1/00* | (2006.01) |
| *A61N 1/372* | (2006.01) |
| *A61N 1/378* | (2006.01) |
| *A61N 1/05* | (2006.01) |
| *A61N 1/36* | (2006.01) |

(52) U.S. Cl.
CPC ....... *A61N 1/37223* (2013.01); *A61N 1/3787* (2013.01); *A61N 1/0541* (2013.01); *A61N 1/36032* (2013.01)

(58) Field of Classification Search
CPC .... A61N 1/36032; A61N 1/0541; A61N 1/08; A61F 11/04; H04R 25/606
USPC ..................... 607/55–57, 136, 137
See application file for complete search history.

(56) References Cited

U.S. PATENT DOCUMENTS

| | | | | |
|---|---|---|---|---|
| 4,532,930 A | * | 8/1985 | Crosby et al. | 607/57 |
| 4,741,339 A | * | 5/1988 | Harrison et al. | 607/2 |
| 4,966,164 A | * | 10/1990 | Colsen et al. | 607/72 |
| 6,067,474 A | | 5/2000 | Schulman et al. | |
| 6,272,382 B1 | * | 8/2001 | Faltys et al. | 607/57 |
| 6,394,947 B1 | * | 5/2002 | Leysieffer | 600/25 |
| 7,054,691 B1 | | 5/2006 | Kuzma et al. | |
| 7,110,822 B1 | | 9/2006 | Palmer | |
| 2003/0212440 A1 | * | 11/2003 | Boveja | 607/46 |
| 2004/0039423 A1 | * | 2/2004 | Dolgin | 607/27 |
| 2005/0015133 A1 | * | 1/2005 | Ibrahim et al. | 607/137 |
| 2011/0046730 A1 | | 2/2011 | Meskens | |
| 2012/0109256 A1 | | 5/2012 | Meskins et al. | |

FOREIGN PATENT DOCUMENTS

| | | |
|---|---|---|
| JP | 2001511409 A | 8/2001 |
| JP | 2002518963 A | 6/2002 |

OTHER PUBLICATIONS

Written Opinion and International Search Report for PCT/IB2013/056006 dated Mar. 13, 2014.

* cited by examiner

*Primary Examiner* — Lindsey G Hankins

(57) ABSTRACT

A total implantable hearing aid system is described. The system includes a single transformer that acts as an insulator between simulation circuitry and associated electrodes, and other system elements residing in the tissue. These other system elements include an RF receiver coil, a microphone system, a battery, and a digital signal processor. The transformer also increases the battery output voltage to a level needed by the simulation circuitry with electrodes.

25 Claims, 4 Drawing Sheets ic # ELECTRICAL ISOLATION IN AN IMPLANTABLE DEVICE

BACKGROUND

Various types of hearing prostheses provide persons with different types of hearing loss with the ability to perceive sound. Hearing loss may be conductive, sensorineural, or some combination of both conductive and sensorineural hearing loss. Conductive hearing loss typically results from a dysfunction in any of the mechanisms that ordinarily conduct sound waves through the outer ear, the eardrum, or the bones of the middle ear. Sensorineural hearing loss typically results from a dysfunction in the inner ear, including the cochlea where sound vibrations are converted into neural signals, or any other part of the ear, auditory nerve, or brain that may process the neural signals.

Persons with certain forms of conductive hearing loss may benefit from hearing prostheses, such as acoustic hearing aids or vibration-based hearing aids. An acoustic hearing aid typically includes a small microphone to detect sound, an amplifier to amplify certain portions of the detected sound, and a small speaker to transmit the amplified sounds into the person's ear. Vibration-based hearing aids typically include a small microphone to detect sound, and a vibration mechanism to apply vibrations corresponding to the detected sound to a person's bone, thereby causing vibrations in the person's inner ear, thus bypassing the person's auditory canal and middle ear.

Persons with certain forms of sensorineural hearing loss may benefit from cochlear implants and/or auditory brainstem implants. For example, cochlear implants provide a person having sensorineural hearing loss with the ability to perceive sound by stimulating the person's auditory nerve via an electrode array implanted in the person's cochlea. In traditional cochlear implant systems, an external component of the cochlear implant detects sound waves, which are converted into a series of electrical stimulation signals delivered to the implant recipient's cochlea via the electrode array. Electrically stimulating auditory nerves in a cochlea with a cochlear implant enables persons with sensorineural hearing loss to perceive sound.

A traditional cochlear implant system includes an external speech processor unit worn on the body of a prosthesis recipient and a stimulator unit implanted in the mastoid bone of the recipient. In this traditional configuration, the external speech processor unit detects external sound and converts the detected sound into a coded signal through a suitable speech processing strategy. The coded signal is sent to the implanted stimulator unit via a transcutaneous link. The stimulator unit (i) processes the coded signal, (ii) generates a series of stimulation signals based on the coded signal, and (iii) applies the stimulation signals to the recipient's auditory nerve via electrodes.

In another example cochlear implant, the functionality of the external speech processor unit and the implanted stimulator unit are combined to create a totally implantable cochlear implant (TICI). The TICI system can be either a monolithic system containing all of the components within a single implant housing or a collection of implant housings coupled together. In operation, detected sound is processed by a speech processor in the TICI system, and stimulation signals are delivered to the recipient via the electrodes without the need for a transcutaneous transmission of signals between an external speech processor unit and an implanted stimulator unit as in the traditional cochlear implant configuration described previously.

SUMMARY

A prosthesis implanted in a body is described. The prosthesis includes a rechargeable energy source, an implant coil that recharges the energy source, a stimulation decoder that provides an output to a hearing stimulator, and a single transformer. The single transformer electrically isolates the implant coil from the stimulation decoder and the hearing stimulator, and modifies an output of the rechargeable energy source for use by the stimulation decoder and the hearing stimulator.

A totally implantable prosthesis is also described. The totally implantable prosthesis includes a first circuit block containing a power source and a converter circuit, a second circuit block containing a stimulation decoder circuit for stimulating electrodes, and a single transformer. The single transformer provides electrical isolation between the first circuit block and the second circuit block. The single transformer also modifies the voltage from the power source to the second circuit block.

An active medical implant device (AIMD) is also described. The AIMD includes a main implant component. The main implant component includes a first circuit separated from a second circuit with a single transformer. The AIMD also includes an implant coil connected to the main implant component, a microphone system connected to the first circuit and a cochlear electrode connected to the second circuit. The transformer prevents AC and DC leakage from the cochlear electrode to the implant coil, the microphone system and the first circuit. The transformer also modifies a voltage from the first circuit to the second circuit. The main implant component, the implant coil, and the microphone reside inside a recipient's tissue after implantation.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE DRAWINGS

Presently preferred embodiments are described below in conjunction with the appended drawing figures, wherein like reference numerals refer to like elements in the various figures, and wherein.

DETAILED DESCRIPTION

Figure 1:
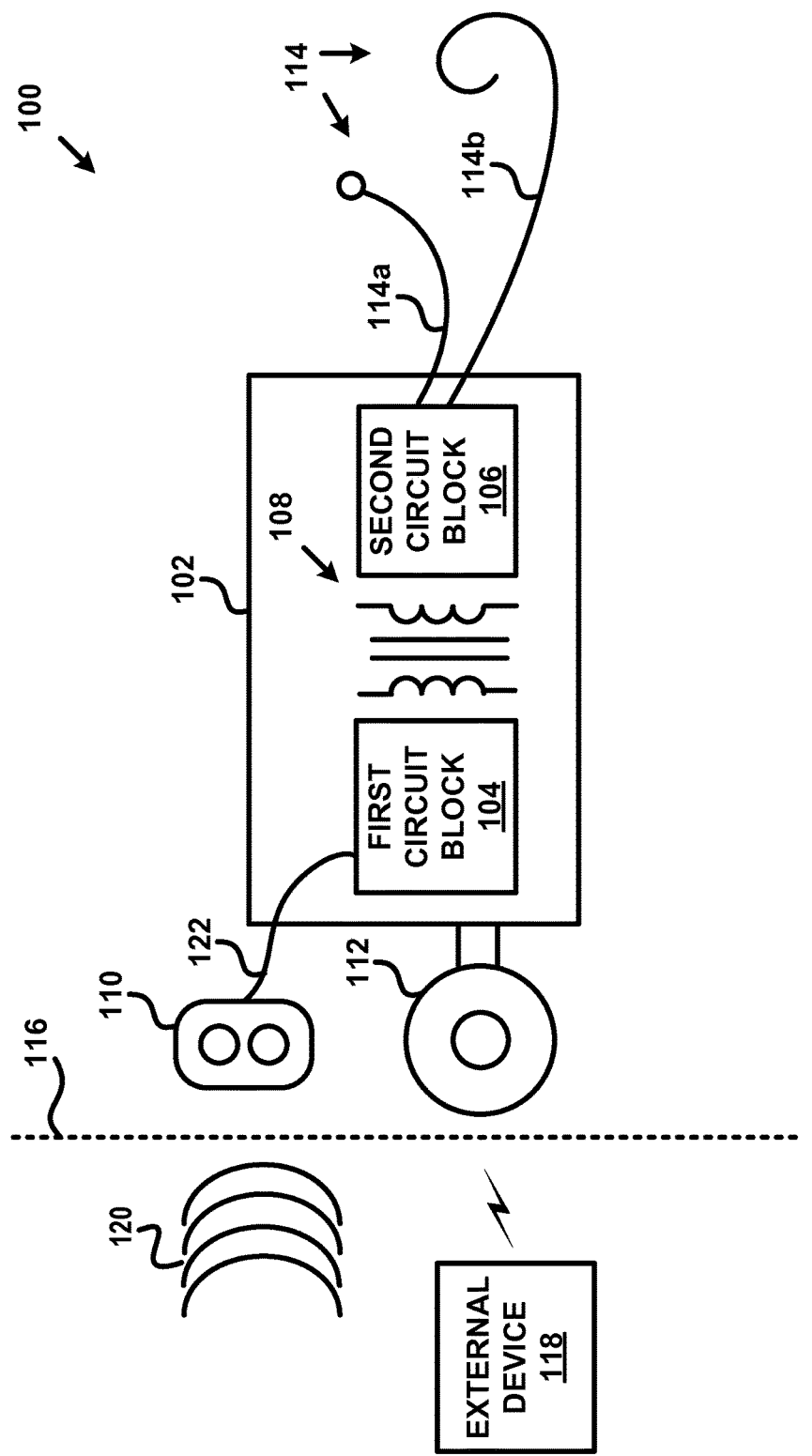
FIG. 1 is a block diagram of a totally implantable cochlear implant (TICI) system, according to an example.

FIG. 1 shows an example of a totally implantable cochlear implant (TICI) system 100, which is totally implantable; that is, all of the components of the TICI system 100 are configured to be implanted under skin/tissue 116 of a recipient. Because all of the components of the TICI system 100 are implantable, the TICI system 100 operates, for at least a finite period of time, without the need of an external device.

An external device 118 can be used to charge an internal energy source and to supplement the performance of the TICI system 100. The external device 118 may be a dedicated charger, a conventional cochlear implant sound processor, a remote control, or other device. In one example, the external device 118 is a Behind the Ear (BTE) headpiece coil, including an external microphone. Various types of energy transfer, such as infrared, electromagnetic, capacitive, and inductive transfer, may be used to transfer power and/or data from the external device 118 to the TICI system 100.

The TICI system 100 includes a microphone 110. The microphone 110 is configured to sense a sound signal 120. The microphone 110 may also include one or more components to pre-process the microphone output. An electrical signal 122 representing the sound signal 120 detected by the microphone 110 is provided to the main implantable component 102.

The TICI system 100 also includes an implant coil 112. The implant coil 112 transcutaneously receives power and data signals from the external device 118 using one or more types of wireless transmission. For example, radio frequency (RF) links may be used to transmit power and data to the implant coil 112. The implant coil 112 may also transmit data signals to the external device 118. The implant coil 112 receives power in a recharging mode of operation.

The implant coil 112 is typically a wire antenna coil comprised of multiple turns of electrically insulated single-strand or multi-strand platinum or gold wire. The implant coil 112 may be produced using a silicone molding process, which can provide additional electrical insulation. Other coil designs may be used.

The TICI system 100 also includes a main implantable component 102 having a hermetically sealed, biocompatible housing. For example, the biocompatible housing can be constructed of a metal, metal alloy, ceramic, peek polymers, or other suitable material. The housing protects the recipient of the TICI system 100 both chemically and electrically.

The main implantable component 102 performs sound detection, speech processing, and stimulation functions. As seen in FIG. 1, the main implantable component 102 includes a first circuit block 104 isolated from a second circuit block 106 via a single transformer 108. If the housing material is magnetically (H-field) or electromagnetically (EM-field) transparent at the operating radio frequency, the implant coil 112 may also be located within the main implantable component 102. For example, a housing material of ceramic or peek polymer may be suitable for containing the implant coil 112 within the main implantable component 102.

The first circuit block 104 includes a rechargeable energy source. In one example, the rechargeable energy source is a battery, such as a lithium ion battery. The rechargeable energy source receives power from the implant coil 112 and stores the power. The output of the rechargeable energy source may be a DC voltage source or a DC current source. The power may then be distributed to the other components of the TICI system 100 as needed for operation.

The first circuit block 104 also includes a converter circuit. The converter circuit implements one or more speech processing and/or coding strategies to convert the pre-processed microphone output into data signals for use by a stimulation decoder circuit in the second circuit block 106. Speech coding strategies include, but are not limited to, Continuous Interleaved Sampling (CIS), Spectral PEAK Extraction (SPEAK), Advanced Combination Encoders (ACE), and Fundamental Asynchronous Stimulus Timing (FAST).

The second circuit block 106 includes the stimulation decoder circuit that generates stimulation signals based on the coded signal received from the converter circuit in the first circuit block 104 and provides these signals to a hearing stimulator. The hearing stimulator delivers electrical stimulation signals to the cochlea of the recipient. In one example, the hearing stimulator is an electrode array 114.

The electrode array 114 includes a plurality of intra-cochlear electrode pads or terminals 114b configured to be positioned within the implant recipient's cochlea, and one or more extra-cochlear electrodes 114a. The intra-cochlear electrode pads or terminals 114b may include optical contacts and/or electrical contacts. The extra-cochlear electrode 114a has an extra-cochlear electrode lead terminating in an electrode tip (sometimes referred to as a "ball" electrode) at the distal end of the electrode lead. The electrode tip is configured to be positioned beneath muscle tissue near the implant recipient's cochlea. The intra-cochlear electrode pads or terminals 114b are typically configured to function as "active" (current source) electrodes, and the one or more extra-cochlear electrodes 114a are typically configured to function as "reference" (current sink) electrodes.

The transformer 108 is a radio frequency (RF) transformer. The transformer 108 acts as an insulator between the electrodes 114 and other system elements residing in the tissue, such as the implantable microphone system 110, the implant coil 112, and components within the first circuit block 104 (e.g., the rechargeable energy source). In this role, the transformer 108 prevents electrical (e.g., AC and DC) leakage between the electrodes 114 and the other implantable system elements.

Stimulation of tissues and nerves using alternating electrical currents passing through tissue can cause problems for the recipient. For example, excess DC currents can cause electrolysis, redox reactions, and chemical reactions. The transformer 108 reduces electrical leakage, which minimizes negative side effects caused by electrical leakage.

The transformer 108 also acts as a voltage boost element providing a boost to the energy source output voltage. The transformer 108 modifies a compliance voltage as necessary to provide the correct stimulation current on each electrode 114 based upon an auditory stimulation algorithm or scheme that controls the timing and intensity of auditory stimulation pulses applied to the electrodes 114. The compliance voltage is the voltage available at the electrode 114 that can force current to flow while still maintaining control of the working electrode voltage.

In this role, the transformer 108 is a part of a step-up DC/DC converter. The energy source output voltages are often lower than the electrode compliance voltage needed for correct operation of the electrode current sources. The compliance voltage of the electrode current sources depends on the impedance between the intra-cochlear electrodes 114b and the extra-cochlear electrodes 114a.

For example, if the impedance is 10 Kohms and the current source is 0.5 mA, the compliance voltage needs to be slightly greater than 5V (i.e., 10 Kohm*0.5 mA=5V). If the energy source is a lithium ion battery, the output voltage is approximately 3.7 volts. Thus, the transformer 108 boosts the lithium ion battery output of 3.7 volts to a value greater than 5 volts.

Using the transformer 108 in this manner provides tight coupling with minimal efficiency losses. By placing the energy source on the primary side of the transformer 108 and the stimulation decoder circuit on the secondary side of the transformer 108, the transformer 108 provides step-up voltage control. Moreover, the transformer 108 prevents or reduces leakage between the electrode array 114 and other TICI system 100 components, such as the microphone 110, the implant coil 112, and components within the first circuit block 104.

Figure 2:
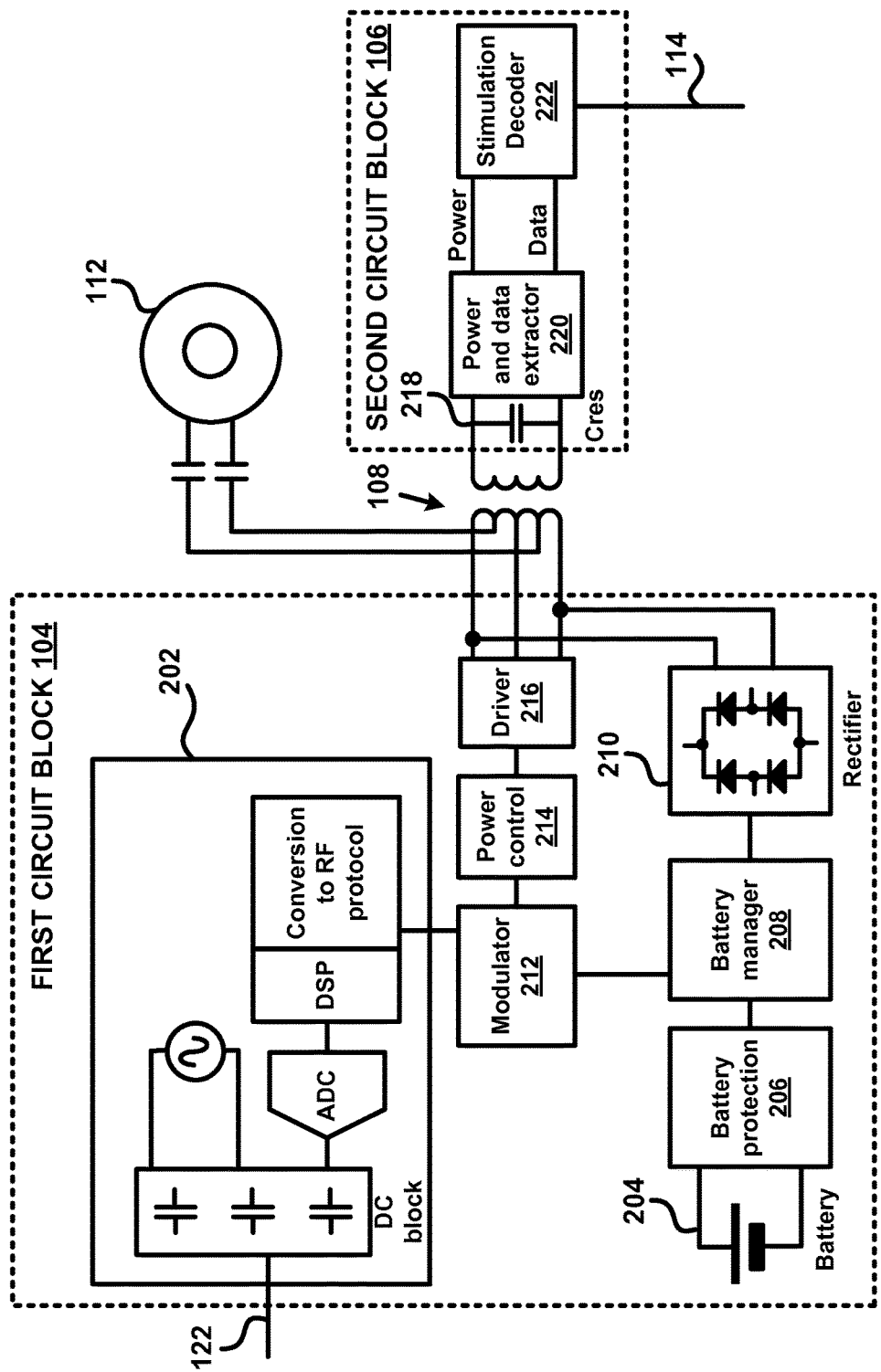
FIG. 2 is a block diagram of a main implantable component depicted in FIG. 1, according to an example.

FIG. 2 is a block diagram of the main implantable component 102, according to an example. As previously seen in FIG. 1, the main implantable component 102 includes the first circuit block 104 isolated from the second circuit block 106 via the single transformer 108. The implant coil 112 is connected to the primary side of the transformer 108.

In this example, the first circuit block 104 includes a converter circuit 202, a battery 204, and additional power circuitry. The converter circuit 202 is an audio to radio frequency stimulation converter. The additional power circuitry includes battery protection 206, a battery manager 208, a rectifier 210, a modulator 212, a power control block 214, and a driver 216. The second circuit block 106 includes a capacitor 218, a power and data extractor 220, and a stimulation decoder 222.

Figure 3:
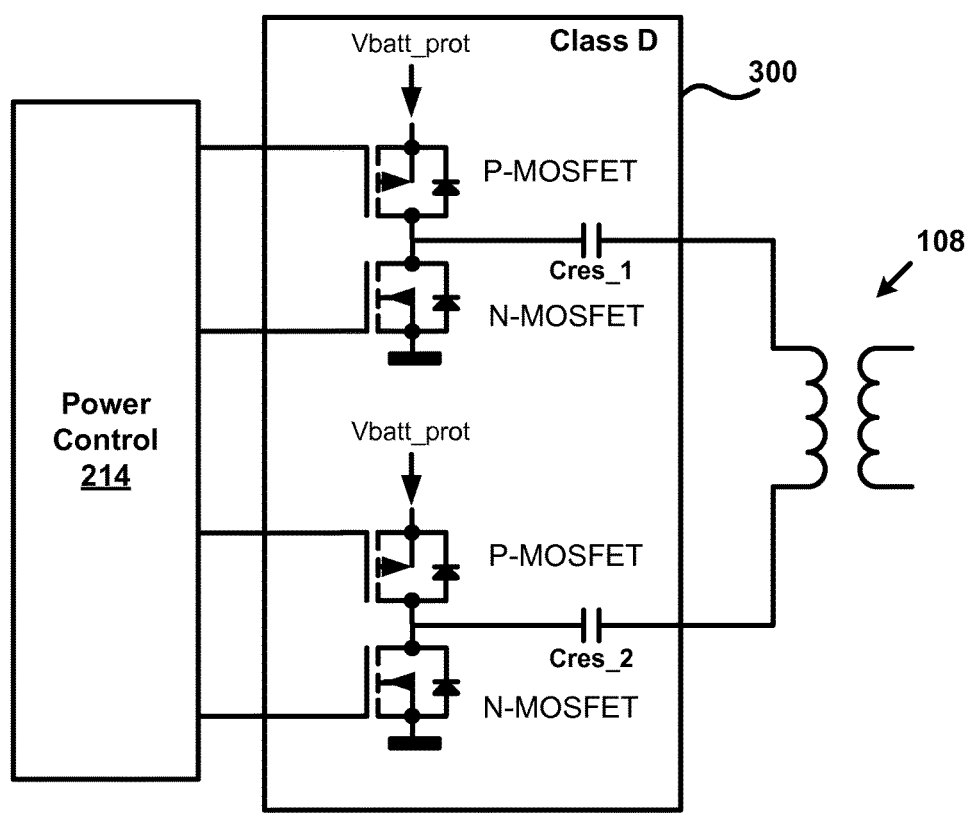
FIG. 3 is a circuit diagram of a Class D driver, according to an example.
Figure 4:
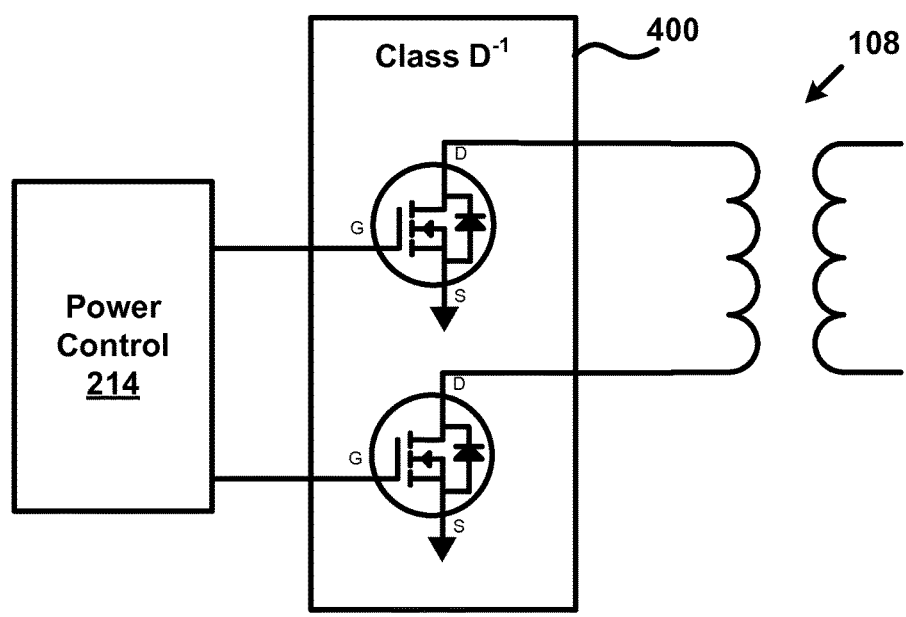
FIG. 4 is a circuit diagram of an inverted Class D Driver, according to an example.

The driver 216 operates in Class-D or inverted Class-D (Class $D^{-1}$) mode delivering power and stimulation data from the microphone 110 and implant battery 204 to the transformer 108. FIG. 3 depicts a Class-D driver 300, while FIG. 4 depicts an inverted Class-D driver 400.

Operation Mode 1: Charging

During charging, a signal from the external device 118 delivers stimulation data to the stimulation decoder 222, and power to the implant battery 204 and the stimulation decoder 222. The power delivered to the battery 204 is used to recharge the battery 204.

With the Class-D driver 300, the N-MOSFETS of the Class-D (Class D1 and Class D2 driver) H-bridge driver are both closed, and parallel resonance is obtained by Cres_1 and Cres_2 (e.g., 5 MHz). The battery 204 can be charged using the rectifier 210 and the battery manager 208. From the perspective of the stimulation decoder 222, the transformer 108 is part of a parallel resonance tank formed by Cres_1 and Cres_2 in series and the inductance of the implant coil 112. The implant coil 112 is scaled by the primary-secondary ratio of the transformer 108.

With the inverted Class-D driver 400, both MOSFETs are open and parallel resonance is obtained with Cres 218 (e.g., at 5 MHz). The battery 204 can be charged using the rectifier 210 and the battery manager 208. From the perspective of the stimulation decoder 222, the transformer 108 is part of a parallel resonance tank formed by Cres 218 and the inductance of the implant coil 112. The implant coil 112 is scaled by the primary-secondary ratio of the transformer 108.

Operation Mode 2: Normal Operations (Charged)

During normal operation when the battery is charged, the converter circuit 202 converts the microphone signal 122 to stimulation data. The stimulation data is then transferred to the modulator 212. Preferably, the modulator 212 is an on-off keying (OOK) modulator. The modulator 212 may use other modulations schemes, such as Amplitude Shift Keying (ASK), Continuous Phase Frequency Shift Keying (CPFSK), Binary Phase Shift Keying (BPSK), and Quadrature Phase-Shift Keying (QPSK).

The power control block 214 controls power to the stimulation decoder 222 and the stimulation compliance voltage. The power control block 214 controls power and the stimulation compliance voltage by adjusting the duty cycle of RF frames and RF cycles. For example, the power control block 214 may use pulse width modulation (PWM) to adjust the duty cycle of the RF frames and RF cycles.

For the Class-D driver 300, the impedance seen from the Class-D driver side is a series resonance circuit formed by Cres_1 and Cres_2 in series and the inductance of the implant coil 112 scaled by the primary-secondary ratio of the transformer 108. The impedance seen from the stimulation decoder 222 is a parallel resonance tank formed by Cres_1 and Cres_2 in series and the inductance of the implant coil 112 scaled by the primary-secondary ratio of the RF transformer 108.

The inverted Class-D driver 400 is powered through the transformer 108 center tap via the rfc coil (RF choke) forming a current source. From the perspective of the stimulation decoder 222, the transformer 108 is part of a parallel resonance tank formed by Cres 218 and the inductance of the implant coil 112. The implant coil 112 is scaled by the primary-secondary ratio of the transformer 108.

As described, the single transformer 108 is used as both an AC/DC barrier and a step-up converter. More than one transformer would increase the volume needed for the implant housing. The transformer 108 is part of a resonant tank circuit built by the implant coil 112 and one or more capacitors.

Another benefit of this single transformer design is the ability to monitor the quality of the microphone 110. During normal operating mode, the external device 118 can monitor the quality of the microphone 110 by using the implant coil 112 to transfer stimulation data from the microphone 110 to the external device 118 through the implant coil 112 once the Class-D driver 300 or the inverted Class-D driver 400 is activated. In this scenario, the external device 118 is connected to an external coil that is magnetically coupled to the implant coil 112.

As yet another benefit of this single transformer design is the ability to use a conventional RF link when the rechargeable energy source is faulty or dead.

In an alternative design, the transformer 108 is used as an insulator between the implant coil 112 and the electrodes 114, and other circuitry is used for the step-up converter function. For example, this additional circuitry can include a boost converter to increase voltage at the current sources of the electrodes 114. The boost converter is an active circuit containing at least an inductor and two capacitors.

In another alternative design, the RF transformer 108 provides insulation between the implant coil 112 and the electrodes 114, and a two-wire transformer provides insulation between the rechargeable energy source and the microphone 110, and the electrodes 114. While this alternative includes two transformers, a single RF transformer reduces the implant housing volume as compared to a design containing two RF transformers.

It is intended that the foregoing detailed description be regarded as illustrative rather than limiting and that it is understood that the following claims including all equivalents are intended to define the scope of the invention. The claims should not be read as limited to the described order or elements unless stated to that effect. Therefore, all embodiments that come within the scope of the following claims and equivalents thereto are claimed as the invention.

What is claimed is:

1. An implantable component of a hearing prosthesis, the implantable component comprising:
   an implant coil;
   a housing configured to be implanted in a recipient;
   a rechargeable energy source;
   a converter circuit configured to implement one or more speech processing or coding strategies;

a stimulation decoder configured to provide an output to a hearing stimulator that is configured to deliver electrical stimulation signals to a recipient of the hearing prosthesis; and a single transformer having a primary side connected to both the implant coil and the rechargeable energy source such that power received at the implant coil is provided to the rechargeable energy source via the primary side of the single transformer, wherein the single transformer electrically isolates the implant coil from the stimulation decoder and the hearing stimulator, and wherein the single transformer modifies an output of the rechargeable energy source for use by the stimulation decoder and the hearing stimulator, and wherein the stimulation decoder is connected to a secondary side of the single transformer so as to receive signals generated by the converter circuit via the single transformer.

2. The implantable component of claim 1, wherein the rechargeable energy source is a battery.

3. The implantable component of claim 1, wherein the output of the rechargeable energy source is a DC voltage source.

4. The implantable component of claim 1, wherein the output of the rechargeable energy source is a DC current source.

5. The implantable component of claim 1, wherein the implant coil provides data transfer.

6. The implantable component of claim 1, wherein the hearing stimulator includes intra-cochlear electrodes.

7. The implantable component of claim 1, wherein the transformer is part of a step-up DC/DC converter configured to increase a voltage of a DC output of the rechargeable energy source to an electrode compliance voltage for operation of electrodes of the hearing stimulator.

8. The implantable component of claim 1, wherein the transformer is part of a resonance tank.

9. The implantable component of claim 1, wherein the prosthesis includes a microphone, and wherein the transformer electrically isolates the microphone from the stimulation decoder and the hearing stimulator.

10. The implantable component of claim 1, wherein the housing further comprises (i) a driver configured to deliver to the single transformer stimulation data and a power signal from the rechargeable energy source, and (ii) a power controller configured to control power provided to the stimulation decoder.

11. The implantable component of claim 10, wherein the power controller is further configured to control a stimulation compliance voltage by adjusting a duty cycle of at least one of radio frequency frames or radio frequency cycles.

12. The implantable component of claim 10, wherein the driver is a Class D driver.

13. The implantable component of claim 10, wherein the driver is an inverted Class D driver.

14. The implantable component of claim 10, wherein the housing further comprises a modulator for modulating the stimulation data and the power signal.

15. The implantable component of claim 10, wherein the rechargeable energy source is connected to the primary side of the single transformer via one or more components.

16. The implantable component of claim 15, wherein the one or more components include the driver and the power controller.

17. An implantable component of a hearing prosthesis, comprising:

an implant coil;

a rechargeable battery;

a converter circuit configured to implement one or more speech processing or coding strategies;

a stimulation decoder configured to generate electrical stimulation signals for delivery to a recipient of the hearing prosthesis; and a transformer having a primary side connected to both the implant coil and the rechargeable battery such that power received at the implant coil is provided to the rechargeable battery via the primary side of the single transformer, wherein the stimulation decoder is connected to a secondary side of the single transformer and is configured to receive signals generated by the converter circuit via the transformer at an increased than an output voltage of the rechargeable battery.

18. The implantable component of claim 17, further comprising:

a driver configured to deliver to, the transformer, stimulation data and a power signal from the rechargeable battery, and a power controller configured to control power provided to the stimulation decoder.

19. The implantable component of claim 18, wherein the power controller is further configured to control a stimulation compliance voltage by adjusting a duty cycle of at least one of radio frequency frames or radio frequency cycles.

20. The implantable component of claim 18, wherein the driver is a Class D driver.

21. The implantable component of claim 18, wherein the driver is an inverted Class D driver.

22. The implantable component of claim 18, further comprising a modulator for modulating the stimulation data and the power signal.

23. The implantable component of claim 18, wherein the rechargeable battery is connected to the primary side of the single transformer via one or more components.

24. The implantable component of claim 23, wherein the one or more components include the driver and the power controller.

25. The implantable component of claim 17, wherein the transformer electrically isolates the implant coil from the stimulation decoder.

* * * * *

UNITED STATES PATENT AND TRADEMARK OFFICE
CERTIFICATE OF CORRECTION

PATENT NO.        : 9,592,395 B2                                         Page 1 of 1
APPLICATION NO.   : 13/555317
DATED             : March 14, 2017
INVENTOR(S)       : Werner Meskens It is certified that error appears in the above-identified patent and that said Letters Patent is hereby corrected as shown below:

In the Claims

Column 8, Line 27, after the word "increased" please insert -- voltage that is greater --

Signed and Sealed this
Ninth Day of May, 2017

Michelle K. Lee
*Director of the United States Patent and Trademark Office*